US009446151B2

(12) United States Patent
Ansaldi et al.

(10) Patent No.: US 9,446,151 B2
(45) Date of Patent: Sep. 20, 2016

(54) IN VIVO IMAGING OF ENZYMATIC ACTIVITY (75) Inventors: Daniel Ansaldi, Alameda, CA (US); Kevin P. Francis, Alameda, CA (US); Rajendra Singh, San Jose, CA (US); Ning Zhang, Alameda, CA (US)

(73) Assignee: Caliper Life Sciences, Inc., Hopkinton, MA (US)

( * ) Notice: Subject to any disclaimer, the term of this patent is extended or adjusted under 35 U.S.C. 154(b) by 535 days.

(21) Appl. No.: 13/446,274

(22) Filed: Apr. 13, 2012

(65) Prior Publication Data
US 2013/0101511 A1    Apr. 25, 2013

Related U.S. Application Data (60) Provisional application No. 61/517,090, filed on Apr. 13, 2011.

(51) Int. Cl.
A61K 49/00    (2006.01)
B82Y 5/00    (2011.01)

(52) U.S. Cl.
CPC ....... *A61K 49/0013* (2013.01); *A61K 49/0067* (2013.01); *B82Y 5/00* (2013.01); *G01N 2800/7095* (2013.01); *Y10S 977/773* (2013.01); *Y10S 977/927* (2013.01)

(58) Field of Classification Search
CPC .................... A61K 49/0013; A61K 49/0067; B82Y 5/00; G01N 2800/7095; Y10S 977/927; Y10S 977/773
See application file for complete search history.

(56) References Cited

U.S. PATENT DOCUMENTS

| 5,650,135 | A | 7/1997 | Contag et al. |
|---|---|---|---|
| 7,226,752 | B1 * | 6/2007 | Roitman ...................... 435/7.92 |
| 7,449,567 | B2 | 11/2008 | Zhang et al. |
| 2008/0003622 | A1 | 1/2008 | Roitman |
| 2009/0053751 | A1 * | 2/2009 | Magrisso et al. ............... 435/29 |

FOREIGN PATENT DOCUMENTS

| WO | 2006/029302 A2 | 3/2006 |
|---|---|---|
| WO | WO 2010/062787 A1 | 6/2010 |
| WO | WO 2011/034590 A1 | 3/2011 |

OTHER PUBLICATIONS

Alexis, et al., "Factors Affecting the Clearance and Biodistribution of Polymeric Nanoparticles," *Mol. Pharm.* 5:505-515 (2008).
Bruchez, et al., "Semiconductor Nanocrystals as Fluorescent Biological Labels," *Science* 281:2013-2016 (1998).
Chan, et al., "Quantum Dot Bioconjugates for Ultrasensitive Nonisotopic Detection," *Science* 281:2016-2018 (1998).
Frangioni, et al., "In Vivo Near-Infrared Fluorescence Imaging," *Curr. Opin. Chem. Biol.* 7:626-634 (2003).
Gao, et al., "In Vivo Cancer Targeting and Imaging With Semiconductor Quantum Dots," *Nature Biotechnology* 22:969-976 (2004).
Gross, et al., "Bioluminescence Imaging of Myeloperoxidase Activity In Vivo," *Nat Med* 15:455-61 (2009).
Huang, et al., "A Resonance Energy Transfer Between Chemiluminescent Donors and Luminescent Quantum-Dots as Acceptors (CRET)," *Angew Che Int* 45:5140-5143 (2006).
Kiellland, et al., "In Vivo Imaging of Reactive Oxygen and Nitrogen Species in Inflammation Using the Luminescent Probe L-012.," *Free Radic Biol Med* 47:760-766 (2009).
Kim, et al., "Multicenter Phase II Trial of Genexol-PM, A Novel Cremophor-Free, Polymeric Micelle Formulation of Paclitaxel, With Cisplatin in Patients With Advanced Non-Small-Cell Lung Cancer," *Ann. Oncol* 18:2009-2014 (2007).
Medintz, et al, "Quantum Dot Bioconjugates for Imaging, Labelling and Sensing," *Nat Mater* 4:435-446 (2005).
Michalet, et al., "Quantum Dots for Live Cells, In Vivo Imaging, and Diagnostics," *Science* 307:538-544 (2005).
Moghimi, et al., "Long-Circulating and Target-Specific Nanoparticles: Theory to Practice," *Pharmacol. Rev.* 53:283-318 (2001).
Nie, et al., "Nanotechnology Applications in Cancer," *Annu Rev Biomed Eng.* 9:257-288 (2007).
Pinaud, et al., "Bioactivation and Cell Targeting of Semiconductor CDSE/ZNS Nanocrystals With Phytochelatin-Related Peptides," *J. Am. Chem. Soc.* 126:6115-6123 (2004).
Romberg, et al., "Sheddable Coatings for Long-Circulating Nanoparticles," *Pharm. Res.* 25:55-71 (2008).
Schluep, et al., "Preclinical Efficacy of the Camptothecin-Polymer Conjugate IT-101 in Multiple Cancer Models," *Clin. Cancer Res.* 12:1606-1614 (2006).
So, et al., "Self-Illuminating Quantum Dot Conjugates for In Vivo Imaging," *Nat. Biotechnol.* 24:339-343 (2006).
Ward, et al., "Energy Transfer via Protein-Protein Interaction in Renilla Bioluminescence," *Photochemistry and Photobiology* 27:389-396 (1978).
Wu, et al., "Immunofluorescent Labeling of Cancer Marker HER2 and Other Cellular Targets With Semiconductor Quantum Dots," *Nat. Biotechnol.* 21:41-46 (2003).
Xu, et al., "A Bioluminescence Resonance Energy Transfer (BRET) System: Application to Interacting Circadian Clock Proteins," *Proc. Natl. Acad. Sci. USA* 96:151-156 (1999).
Zhang, et al., "Halo Tag Protein-Mediated Site-Specific Conjugation of Bioluminescent Proteins to Quantum Dots," *Angew. Chem. Int.* 45: 4936-4940. (2006).
Zhao, et al., "A Nonenzymatic Chemiluminescent Reaction Enabling Chemiluminescence Resonance Energy Transfer to Quantum Dots," *Chem. Eur. J.* 16: 6142-6145. (2010).
Kosaka, et al., "Self-Illuminating In Vivo Lymphatic Imaging Using a Bioluminescence Resonance Energy Transfer Quantum Dot Nano-Particle," *Contrast Media Mol. Imaging* 6:55-59 (2011).
Ma, et al., "Near-Infrared Light Emitting Luciferase via Biomineralization," *J. Am. Chem. Soc.* 132:6884-6885 (2010).
Zhang, et al., "Enhanced Detection of Myeloperoxidase Activity in Deep Tissues Through Luminescent Excitation of Near-Infrared Nanoparticles," *Nature Medicine* 19(4):500-506 (2013).

* cited by examiner

*Primary Examiner* — Johann R Richter
*Assistant Examiner* — Genevieve S Alley
(74) *Attorney, Agent, or Firm* — Pasternak Patent Law; Dahna S. Pasternak (57) ABSTRACT

Compositions and methods are described for detecting enzyme activity in a live organism (e.g., animal) are provided.

22 Claims, 11 Drawing Sheets

IN VIVO IMAGING OF ENZYMATIC ACTIVITY

CROSS-REFERENCE TO RELATED APPLICATIONS

The present application claims the benefit of U.S. Provisional Application No. 61/517,090, filed Apr. 13, 2011, the disclosure of which is hereby incorporated by reference in its entirety.

TECHNICAL FIELD

The present disclosure is in the field of reagents for use in evaluation of enzymatic activity in a living organism. In particular, described herein are compositions and methods for monitoring enzymatic activity associated with oxidative stress in vivo.

BACKGROUND

Detection of light indicative of enzymatic activity from living organisms is a powerful tool in diagnostics, drug discovery and medicine that allows for the identification of disease pathways, determination of mechanisms of action, evaluation of efficacy of drug compounds, and monitoring lead candidates' effects on disease progression in living animals. For example, imaging myeloperoxidase activity has been described for monitoring oxidative stress. See, e.g., Gross et al. (2009) *Nat Med* 15:455-61; Kielland et al. (2009) *Free Radic Biol Med.* 47:760-6; and International Patent Publication WO 2010/062787). These methods use exogenously supplied luminol to detect invasive reactive oxygen species that are produced during inflammation processes by infiltrating neutrophils and monocytes/macrophages in stressed tissues.

Additional methods for imaging enzyme activity in vivo include bioluminescence resonance energy transfer (BRET) (see, e.g., Ward et al. (1978) *Photochem. Photobiol.* 27:389-396; Xu et al. (1999) *Proc. Natl. Acad. Sci. USA* 96:151-156; So et al. (2006) *Nat. Biotechnol.* 24:339-343) and Fluorescence by Unbound Excitation from Luminescence (FUEL) (see, e.g., Dragavon et al. 2010, Poster presentation at 10th International ELMI Meeting, Heidelberg) which use exogenous enzymes, such as luciferase, for light generation. Fluorescence resonance energy transfer (FRET), which investigates biological phenomena that produce changes in molecular proximity, uses exogenous excitation light.

Under physiological conditions, low levels of reactive oxygen and nitrogen species are generated by the cells and play a critical role in cell signaling and maintenance of vascular homeostasis. During pathological inflammatory responses, large quantity of reactive oxygen species (ROS) are generated by infiltrating neutrophils and monocytes/macrophages of stressed tissues. While there are a number of pathways for ROS production, one of them involves the membrane bound enzyme NADPH oxidase, which is abundant in neutrophils and monocytes/macrophages. Upon stimulation with inflammatory stimuli, the NADPH mediates a respiratory burst and converts $O_2$ to superoxide anion ($O^{\cdot-}$), which is subsequently catalyzed by superoxide dismutase to form hydrogen peroxide ($H_2O_2$). Further reaction of hydrogen peroxide with the chloride anion is catalyzed by myeloperoxidase (MPO) to produce hypochlorous acid (HOCl). In the presence of luminol, oxidation of luminol by hypochlorous acid results in formation of 3-aminophthalate and accompanying light emission. Chemiluminescence light emission generated from this reaction cascade can be exploited as a read-out for superoxide production and myeloperoxidase activity.

However, detecting oxidative stress by imaging the luminol and hypochlorous acid reaction has limited sensitivity due to the short wavelength of the emitted light. Chemiluminescence light from the luminol oxidation reaction has a peak emission at 425 nm. It has been well established that tissue absorption of propagating light by chlorophores such as hemoglobin is most prominent with lower wavelength lights that are in the spectrum of 400-600 nm. As a result, luminol mediated chemiluminescence has limited penetration capability through tissues. Furthermore, there are concerns about immune reactions to the exogenous enzymes used in BRET and FUEL. FRET imaging methods are also problematic in that the exogenous excitation light can cause tissue autofluorescence which interferes with detection.

Therefore, there remains a need for compositions for and methods of monitoring enzymatic activity in living organisms.

SUMMARY

The present invention includes compositions and methods for monitoring enzymatic activity in a living organism (e.g., animal) by coupling a chemiluminescent enzymatic reaction that monitors enzyme activity to near-infrared (NIR) nanoparticles, thereby providing enhanced detection of the enzymatic activity as compared to chemiluminescent probes alone.

Thus, in one aspect, described herein is a composition comprising a chemiluminescent enzymatic probe and a near-infrared (NIR) nanoparticle. In certain embodiments, the chemiluminescent enzymatic probe comprises luminol and/or a derivative of luminol. In any of the compositions described herein, the NIR nanoparticle may further comprise a targeting moiety (e.g., an antibody, an antibody fragment, a small molecule, an apatmer and a polypeptide).

In another aspect, provided herein is a method of monitoring enzymatic activity in a live animal, the method comprising: administering a chemiluminescent probe (e.g., luminol or luminol derivative) to the animal; administering a near-infrared (NIR) nanoparticle to the animal, wherein the nanoparticle emits light (e.g., NIR) upon exposure to the chemiluminescence emitted from the chemiluminescent probe; and detecting the light (e.g., NIR) emitted from the nanoparticle, thereby monitoring enzymatic activity in the live animal. In certain embodiments, ROS activity is monitored to determine enzymatic activity. In any of the methods described herein, detection of light from the nanoparticle is indicative of inflammation (an inflammatory response), for example in the lungs.

In another aspect, provided herein is a method of detecting a tumor in a live animal, the method comprising: administering a chemiluminescent probe (e.g., luminol or luminol derivative) to the animal; administering a near-infrared (NIR) nanoparticle to the animal, wherein the nanoparticle emits light (e.g., NIR) upon exposure to the chemiluminescence emitted from the chemiluminescent probe; and detecting the light (e.g., NIR) emitted from the NIR nanoparticle, thereby detecting a tumor in the live animal. The methods can be used to detect metastases.

These and other embodiments will readily occur to those of skill in the art in view of the disclosure herein.

BRIEF DESCRIPTION OF THE FIGURES

FIG. 1 is a schematic depicting nanoparticle absorbed chemiluminesence (NAC) as described herein. As shown, an exogenous reagent reacts with a product from an enzymatic reaction (substrate acted on by enzyme), resulting in emission of short wavelength light ("hv1"). In the presence of near-infrared (NIR) nanoparticle, short wavelength photons are absorbed and re-emitted by the nanoparticles as red-shifted NIR light ("hV2", for instance in the 700-950 nm range).

FIG. 2, panels A and B, show nanoparticle absorbed chemiluminescence in live animals. FIG. 2A images of mice injected intratracheal with 50 µl of lipopolysaccharide (LPS) at 1 mg/kg. Three hours post-LPS delivery, mice were injected intraveneously with a mixture of L012 and QD800 to achieve a dosage of 50 mg/kg (probe) and 100 pmol (nanoparticle)/mouse, respectively. FIG. 2A shows images of animals (the experimental number of the animal is indicated above each image) and FIG. 2B is a graph depicting quantification of the lung signals. Both imaging and quantification were performed at 5 minutes post injection of the probe.

FIG. 3, panels A to C, depict NAC imaging in lungs of live animals. Animals were divided into three groups of animals. One group of animals was intravenously administered a mixture of luminol and nanoparticles only (4 animals shown in left panels of FIG. 3A labeled "control-luminol-R"). A second group of animals was administered LPS (50 ul at 1 mg/kg) and 3 hours later treated with luminol only (4 animals shown in middle panels of FIG. 3A, labeled "LPS-luminol"). The third group of animals received LPS (50 ul at 1 mg/kg) and, 3 hours later, an intravenous injection of a mixture of luminol and QD800 (dissolved in PBS) to achieve a dosage of 200 mg/kg and 100 pmol/mouse, respectively (4 animals shown in right panels of FIG. 3A labeled "LPS-luminol-R"). FIG. 3A shows images obtained immediately after injection (top panels, labeled T=0) and at 3 hours post LPS with intravenous injection of luminol/nanoparticle and 5 minutes exposure time (bottom panels, labeled T=3 hrs). FIG. 3B is a graph depicting result of lung inflammation assays and shows lung inflammation was detectable only in mice treated with LPS and the luminol/nanoparticles mixture ("LPS+Lum-R"). The left most bar at each time period shows the control; the middle bar shows LPS-luminol treated animals ("LPS+Lum") and the right most bar shows animals treated with LPS and 3 hours later with a mixture of luminol and QD 800 ("LPS+Lum–R"). FIG. 3C is a graph depicting imaging results shown in FIG. 3A.

FIG. 4, panels A and B, depict NAC imaging in lungs of the mice that were injected intratracheal with 50 ul of LPS (1 mg/kg). The numbers above the images of FIG. 4A refer to the number of the animal, with mouse #1 serving as a negative control. At 3 hours post LPS delivery mice were injected intravenously with a mixture of luminol and QD800 (dissolved in PBS) to achieve a dosage of 200 mg/kg and 100 pmol/mouse respectively. To show that the chemiluminescence was red-shifted, imaging was taken with NIR filters (780, 800, 820 nm). FIG. 4A shows images taken of the animals with the indicated filters and demonstrates that red-shifted NIR light was emitted from the lung, with a peak at 800 nm. Using a 500 nm filer, the un-shifted light from luminol can also be detected at lower levels. FIG. 4B is a graph depicting average NAC signal from the indicated animals at the indicated time points with the indicated filters. There are four bars in each condition (time and nanometers). The left most bar in each of the panels shows the control ("1-control") and is at essentially 0 at all conditions. The bar second to the left (cross-hatched) shows animal 5 ("5-Lum-R") at each condition; the bars second from the right (solid) show animal 9 ("9-Lum-R") and the right most bars (horizontal hatching) show animal 10 ("10-Lum-R").

FIG. 5, panels A and B, depict various exemplary formulations of NACs for imaging lung inflammation. Three different nanoparticles were separately formulated with luminol and the working solution are designated luminol-R (luminol-Qdot800), Luminol-R700 (eFluor® 700NC, eBioSciences), and Luminol640 (nanoparticles from Optimeos Life Sciences). Mice were injected intratracheally with 50 ul of LPS (1 mg/kg). At 3 hours post LPS delivery mice were injected intravenously with luminol-R, Luminol-R700, Luminol-640 respectively and imaged for 5 minutes (FIG. 5A, T=3 hrs). FIG. 5B is a graph depicting average NAC signal from the indicated group of animals at the indicated time points.

FIG. 6, panels A to C, are images showing detection of tumor metastases in live animals. A Nu/Nu mouse was intracardiacally injected with 1 million of MDA-MB-231-luc2 cells. At three weeks, the mouse was imaged with an IVIS spectrum following intraperitoneal injection of luciferin (150 mg/kg). Bioluminescent tumor metastases were detected in the lungs, knee joints and cranial region following luciferin injection (FIG. 6A). At 24 hours after luciferin injection when the bioluminescence signal returned to a base line level, this mouse was injected intravenously with luminol. Tumor metastasis at the knee joint was detected following luminol injection (FIG. 6B). After another 24 hours when the signal returned to background level, a mixture of luminol and QD800 (Luminol-R, in PBS) was intravenously injected and the mouse was imaged at 5 minutes after the injection. FIG. 6C shows sensitive detection of the NAC signals in the lungs and knee joint. These signals correlated with tumor metastases in these loci, affirming that the tumor

DETAILED DESCRIPTION

The practice of the present invention will employ, unless otherwise indicated, conventional methods of chemistry, biochemistry, and recombinant DNA techniques, within the skill of the art. Such techniques are explained fully in the literature. See, e.g., A. L. Lehninger, *Biochemistry* (Worth Publishers, Inc., current addition); Sambrook, et al., *Molecular Cloning: A Laboratory Manual* (2nd Edition, 1989); *Short Protocols in Molecular Biology*, 4th ed. (Ausubel et al. eds., 1999, John Wiley & Sons); *Molecular Biology Techniques: An Intensive Laboratory Course*, (Ream et al., eds., 1998, Academic Press); *PCR* (*Introduction to Biotechniques Series*), 2nd ed. (Newton & Graham eds., 1997, Springer Verlag); and *Methods In Enzymology* (S. Colowick and N. Kaplan eds., Academic Press, Inc.).

All publications, patents and patent applications cited herein, whether supra or infra, are hereby incorporated by reference in their entireties.

1. DEFINITIONS

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "a nucleic acid" includes a mixture of two or more such nucleic acids, and the like.

As used herein, "luminescence" refers to the detectable electromagnetic (EM) radiation, generally, UV, IR or visible light that is produced when the excited product of an exergic chemical process reverts to its ground state with the emission of light. "Chemiluminescence" is luminescence that results from a chemical reaction. "Bioluminescence" is chemiluminescence that results from a chemical reaction using biological molecules (or synthetic versions or analogs thereof) as substrates and/or enzymes. Thus, "bioluminescence" refers to the emission of light by biological molecules, particularly proteins. The essential condition for bioluminescence is molecular oxygen, either bound or free in the presence of an oxygenase, a luciferase and ATP, which acts on a substrate, a luciferin. Bioluminescence is generated by an enzyme or other protein (e.g., luciferase) that is an oxygenase that acts on a substrate (e.g., luciferin) and transforms the substrate to an excited state, which upon return to a lower energy level releases the energy in the form of light. Substrates and enzymes for producing bioluminescence, include, for example, luciferin and luciferase, respectively. The luciferin and luciferases may be from any species.

"Light-generating" is defined as capable of generating light through a chemical reaction or through the absorption of radiation.

"Animal" as used herein typically refers to a non-human mammal, including, without limitation, farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

A "transgenic animal" refers to a genetically engineered animal or offspring of genetically engineered animals. A transgenic animal usually contains material from at least one unrelated organism, such as from a virus, plant, or other animal. The "non-human animals" of the invention include vertebrates such as rodents, non-human primates, sheep, dogs, cows, amphibians, birds, fish, insects, reptiles, etc. The term "chimeric animal" is used to refer to animals in which the heterologous gene is found, or in which the heterologous gene is expressed in some but not all cells of the animal.

2. GENERAL

Before describing the compositions and methods in detail, it is to be understood that the disclosure is not limited to particular formulations or process parameters as such may, of course, vary. It is also to be understood that the terminology used herein is for the purpose of describing particular embodiments only, and is not intended to be limiting.

Although a number of methods and materials similar or equivalent to those described herein can be used, exemplary preferred materials and methods are described herein.

The present disclosure relates to compositions and methods comprising a chemiluminescent enzymatic probe in combination with a NIR nanoparticle. The NIR nanoparticle red-shifts the light produced by the chemiluminescent probe for enhanced detection of enzymatic activity in vivo. This nanoparticle absorbed chemiluminescence (referred to as "NAC") can serve as a readout for enzymatic activity (e.g., ROS production).

The NAC compositions and methods described allow for the highly sensitive detection of enzyme activity in vivo without the use of exogenous enzymes (e.g., as required in BRET or FUEL), thereby reducing or eliminating the potential immune response in the host animal to exogenous enzymes. Likewise NAC compositions and methods do not require exogenous excitation light and, accordingly, bypass the perturbance of tissue autofluorescence, which constitutes a major obstacle for detectability.

Thus, NAC compositions can successfully detect a product from an endogenous enzymatic reaction using a mixture of a chemiluminescent probe (e.g., luminol) and NIR nanoparticles and is useful in detection of a broad range of disease, including various lung inflammation conditions (chronic obstructive pulmonary diseases, asthma), atherosclerosis, arthritis, tumor development, sepsis and infectious diseases. As no toxicity has been detected with chemiluminescent probes or nanoparticles (Schluep et al. (2006) *Clin. Cancer Res.* 12:1606-1614; Kim et al. (2007) *Ann. Oncol.* 18:2009-2014; Romberg et al. (2008) Pharm. Res. 25:55-71; Moghimi et al. (2001) *Pharmacol. Rev.* 53:283-318), the compositions and methods described are also useful for animal studies, including clinical applications.

Reagents

The compositions described herein include both a chemiluminescent probe (e.g., luminol) and a NIR nanoparticle.

Chemiluminescent probes that detect enzymatic activity are well known in the art and are commercially available. Non-limiting examples of chemiluminescent probes include luminol, lucigenin, trans-1-(2'-Methoxyvinyl)pyrene, coelenterazine, tetrazolium salts (e.g., nitro blue tetrazolium salt), etc. In certain embodiments, the chemiluminescent probe is luminol or a derivative of luminol.

The NAC reagents described herein also comprise a NIR nanoparticle. Any suitable nanoparticle can be used. For example, NIR fluorescent nanoparticles such as quantum dots have been used as imaging trackable targeting probes (Medintz et. al. (2005) *Nat. Mater.* 4:435-446; Pinaud et al. (2004) *J. Am. Chem. Soc.* 126:6115-6123); Wu et al. (2003) *Nat. Biotechnol.* 21:41-46, 2003; Frangioni et al. (2003) *Curr. Opin. Chem. Biol.* 7:626-634; Michalet et al. (2005) *Science* 307:538-544). Fluorescent nanoparticle labeled probes have also been used for tumor targeting and for drug delivery and discovery, with the help of in vivo imaging of for visualizing distribution and targeting process of the fluorescence probes (see, e.g., Nie et al (2007) *Annu Rev Biomed Eng.* 9:257-88). Unlike organic fluorophores that have close proximity of optimal absorption and emission spectrums, fluorescent nanoparticles can be excited by broad continuous spectra of photons that are shorter than the optimal emission light to generate red-shifted light emission with high quantum yield (see, e.g., Bruchez et al. (1998) *Science* 281:2013-201; Chan et al. (1998) Science 281: 2016-2018. In fact, fluorescent nanocrystal's blue-increasing extinction coefficient allows NIR crystals being efficiently excited with shorter wavelength blue light. Thus, capturing luminol emitted blue light with fluorescent nanoparticles and red-shifting it to NIR light increases sensitivity of imaging detection due to both high quantum yield of energy transfer and better tissue penetration capability of the NIR light.

Figure 5A:
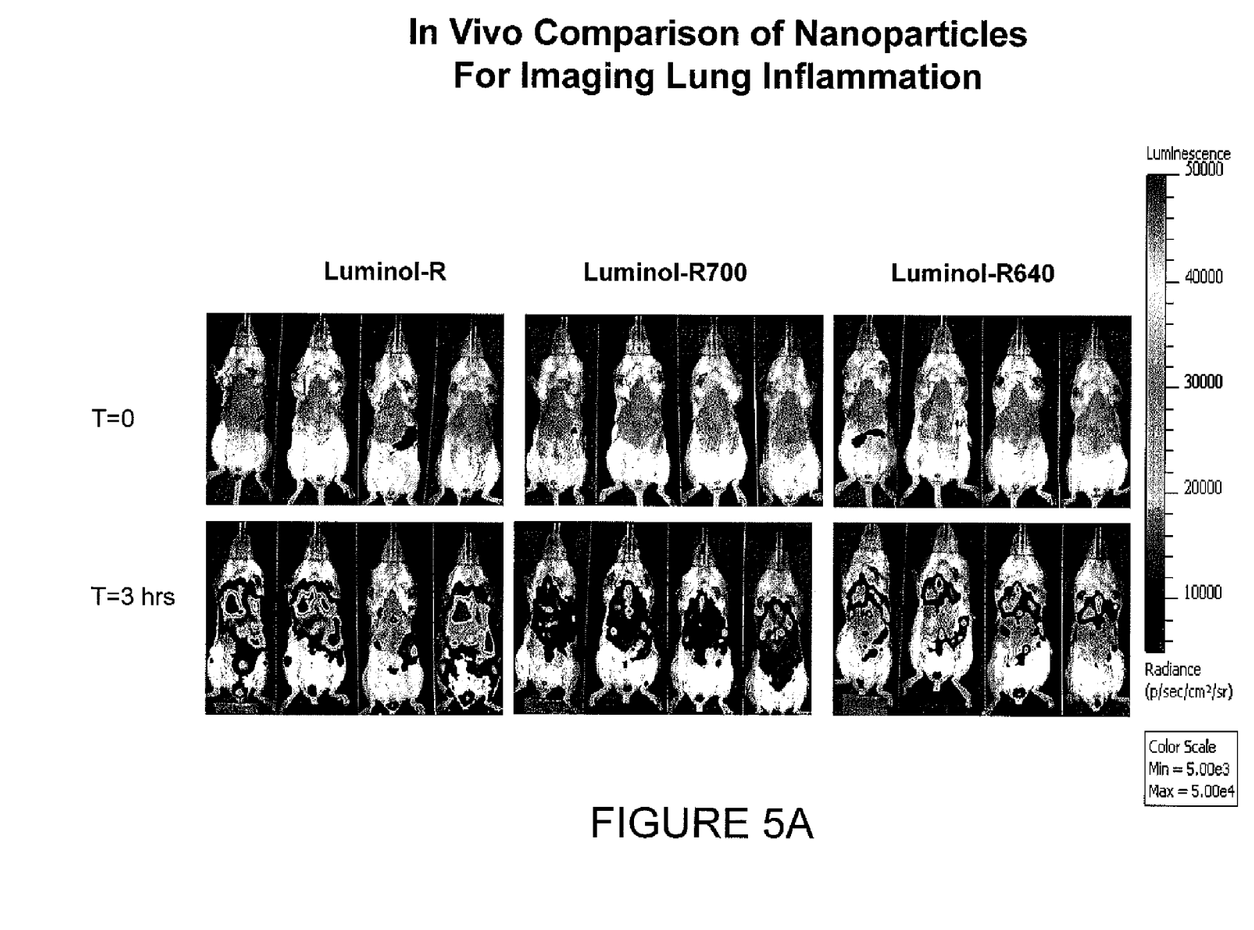
Figure 5B:
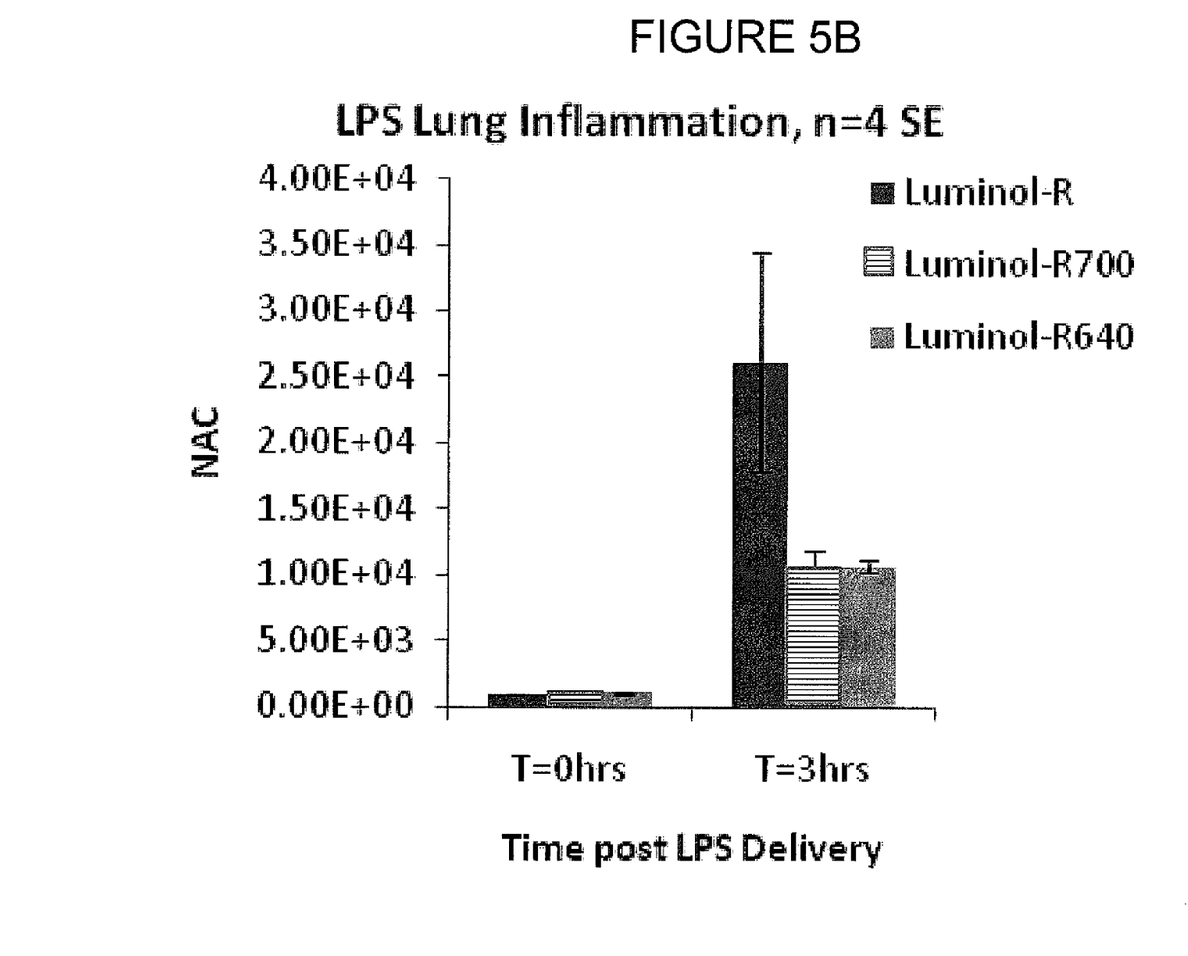

Non-limiting examples of suitable NAC reagents include, but are not limited to luminol-Qdot800, Luminol-700 (containing eFluor® 700NC from eBioscience) and luminol-R640 (containing nanoparticles from Optimeos). See, also, FIG. 5.

The NIR nanoparticles are preferably targeted to particular tissues. Non-limiting examples of targeting moieties include ligands conjugated to the surface of nanoparticles. These ligands include, but are not limited to, antibodies, engineered antibody fragments, proteins, peptides, small molecules, and aptamers (Alexis et al. (2008) *Mol. Pharm.* 5:505-515.

The NIR nanoparticles and chemiluminescent probes can be administered concurrently or sequentially (in any order).

Imaging

Animals treated with the NAC as described herein are conveniently imaged as described in U.S. Pat. Nos. 5,650,135 and 7,449,567 and as described in the materials provided by the manufacturer of the IVIS™ imaging systems, Caliper Life Sciences.

In vivo imaging can be performed using the naked eye or any sort for camera (still or video). In certain embodiments, an intensified CCD camera sensitive enough to detect the bioluminescent signal and with wide enough dynamic range to also detect the fluorescent signal is used for imaging. Suitable cameras are known in the art and include, but are not limited to, an integrated imaging system (IVIS™ Imaging System, Caliper Life Sciences) controlled using LivingImage™ software (Caliper Life Sciences).

The chemiluminescent probe and/or NIR nanoparticle is(are) typically injected into the intraperitoneal cavity or intravenously for imaging in live subjects. It will be apparent to the skilled artisan that dosages can be determined based on conditions (e.g., type of subject, etc.). Generally, approximately 10-300 mg/kg (or any value therebetween) of probe and 10-100 pmol (or any value therebetween) of nanoparticles are administered for imaging.

Imaging may be performed immediately. Alternatively, imaging may be performed after a period for time (ranging from seconds to minutes to hours). In certain embodiments, the subject(s) is(are) imaged 5 to 10 or 10 to 30 minutes (or any value therebetween) after administration of the probe and/or NIR nanoparticle. In other embodiments, the subject the subject(s) is(are) imaged after 30-60 minutes (or any value therebetween) or longer after administration of the probe and/or NIR nanoparticle. It will also be apparent that multiple images at different time points may be taken.

Kits

The present invention also provides kits comprising the reagents described herein and for carrying out the methods described herein. In particular, these kits typically include a pre-made NAC reagents or individual elements (e.g., NIR nanoparticle, chemiluminescent enzymatic probe, etc.). The kit optionally includes buffers and containers as well as written instructions for carrying out the methods described herein. In the case of prepackaged reagents, the kits optionally include pre-measured or pre-dosed reagents that are ready to incorporate into the methods without measurement, e.g., pre-measured fluid aliquots, or pre-weighed or pre-measured solid reagents that may be easily reconstituted by the end-user of the kit.

3. EXPERIMENTAL

Below are examples of specific embodiments for carrying out the present disclosure. The examples are offered for illustrative purposes only, and are not intended to limit the scope of the present disclosure in any way.

Example 1

Detection of an Acute Inflammatory Response in Pulmonary Tissues

An acute inflammatory response in pulmonary tissues was induced by intratracheal delivery of LPS to mice. In particular, LPS was dissolved in sterile PBS to a concentration of 10 mg/ml. LPS (in 50 µl total volume) was delivered to mice intratracheally with a 22-gauge intubator. The final dose of LPS was 1 mg/kg. Following delivery of LPS, a mixture of luminol and nanoparticles (Quantum dot 800) was delivered to the animals intravenously. Imaging was performed at 5 minutes after injection.

Figure 1:
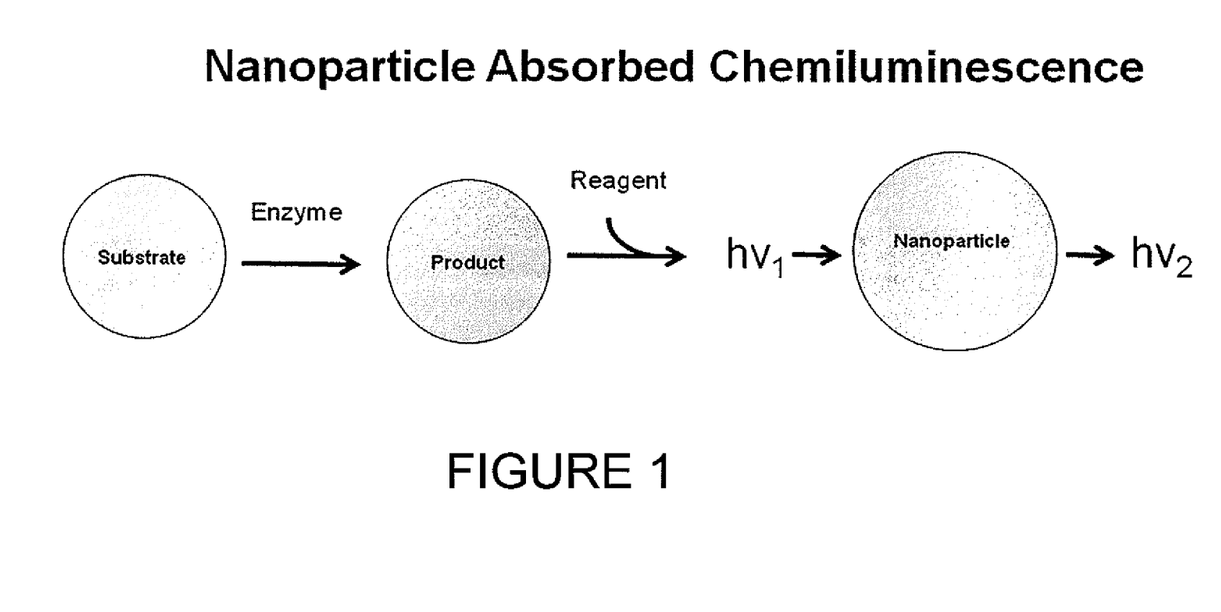
Figure 2A:
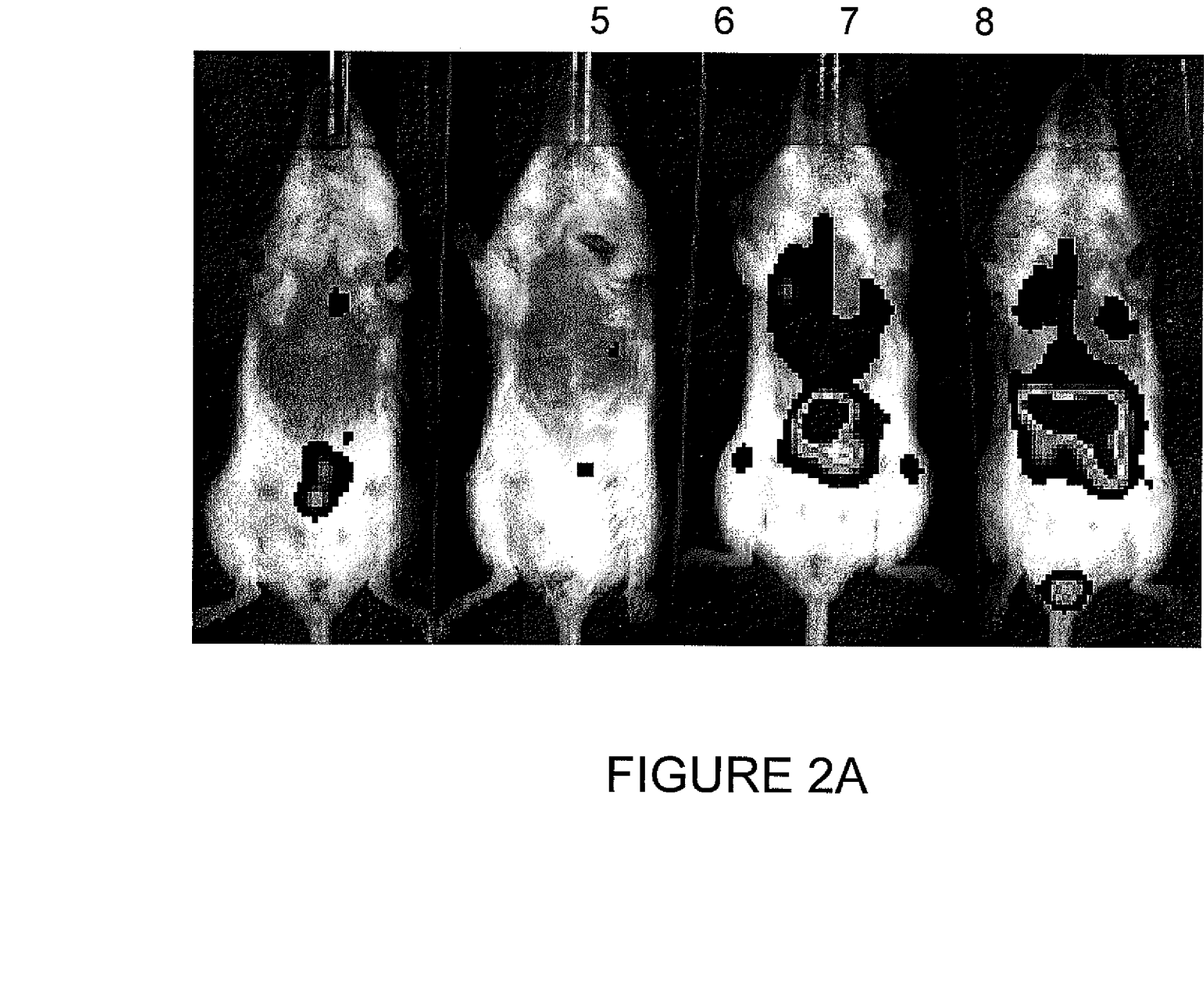
Figure 2B:
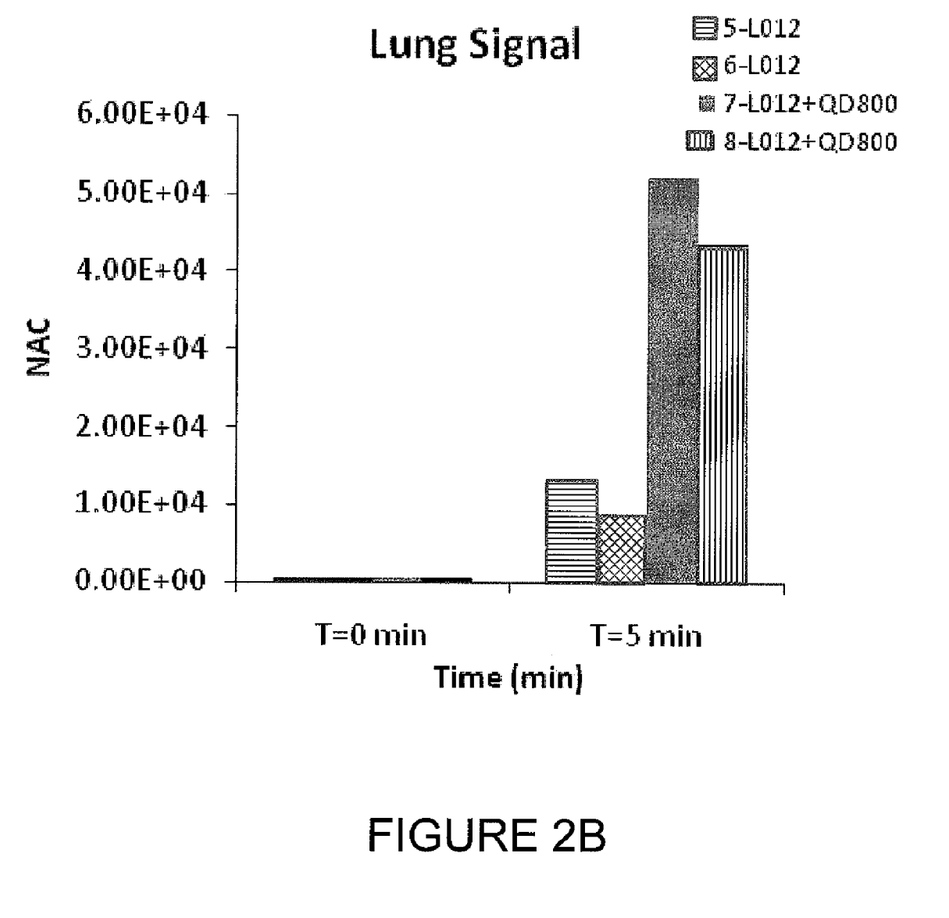
Figure 3A:
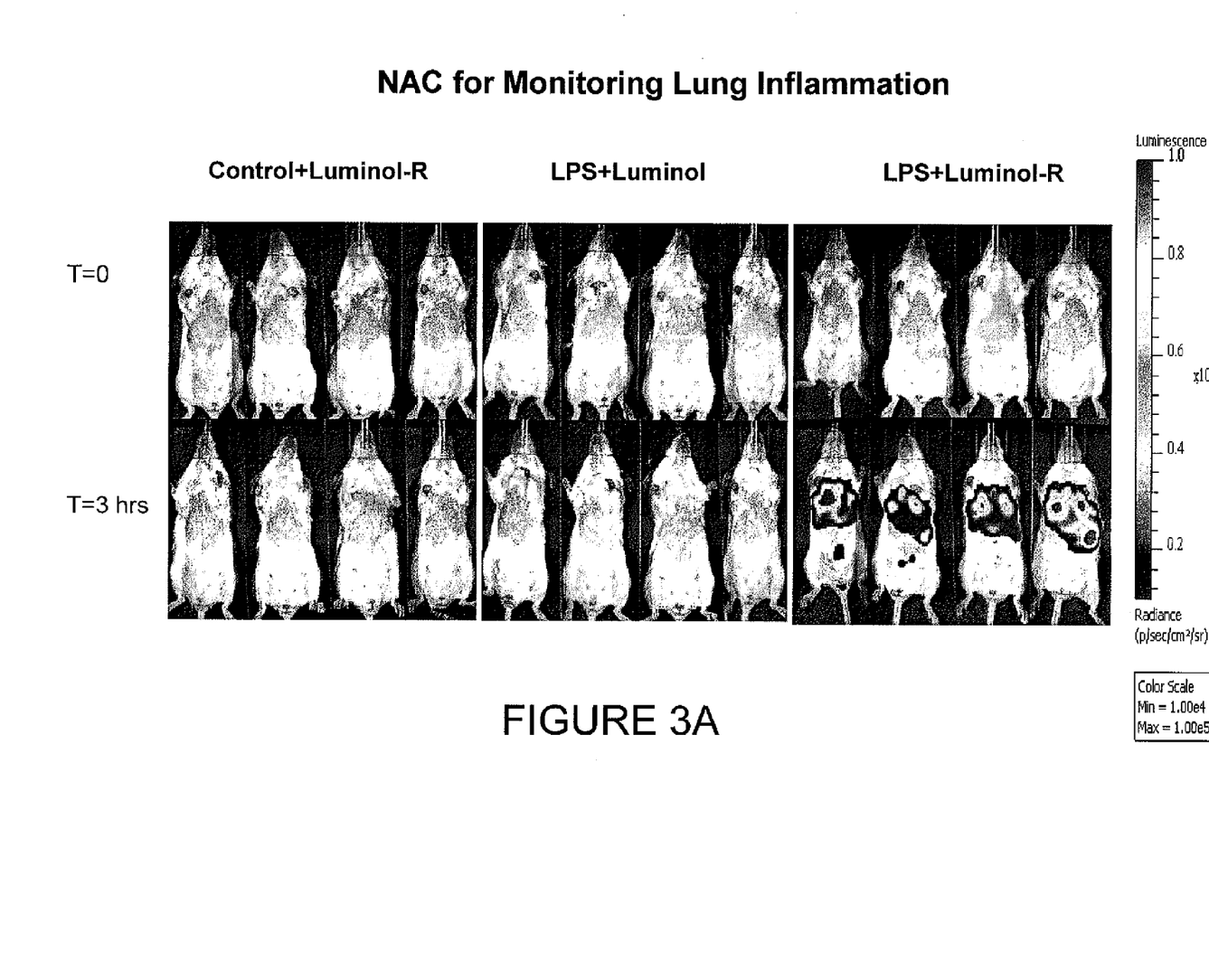
Figure 3B:
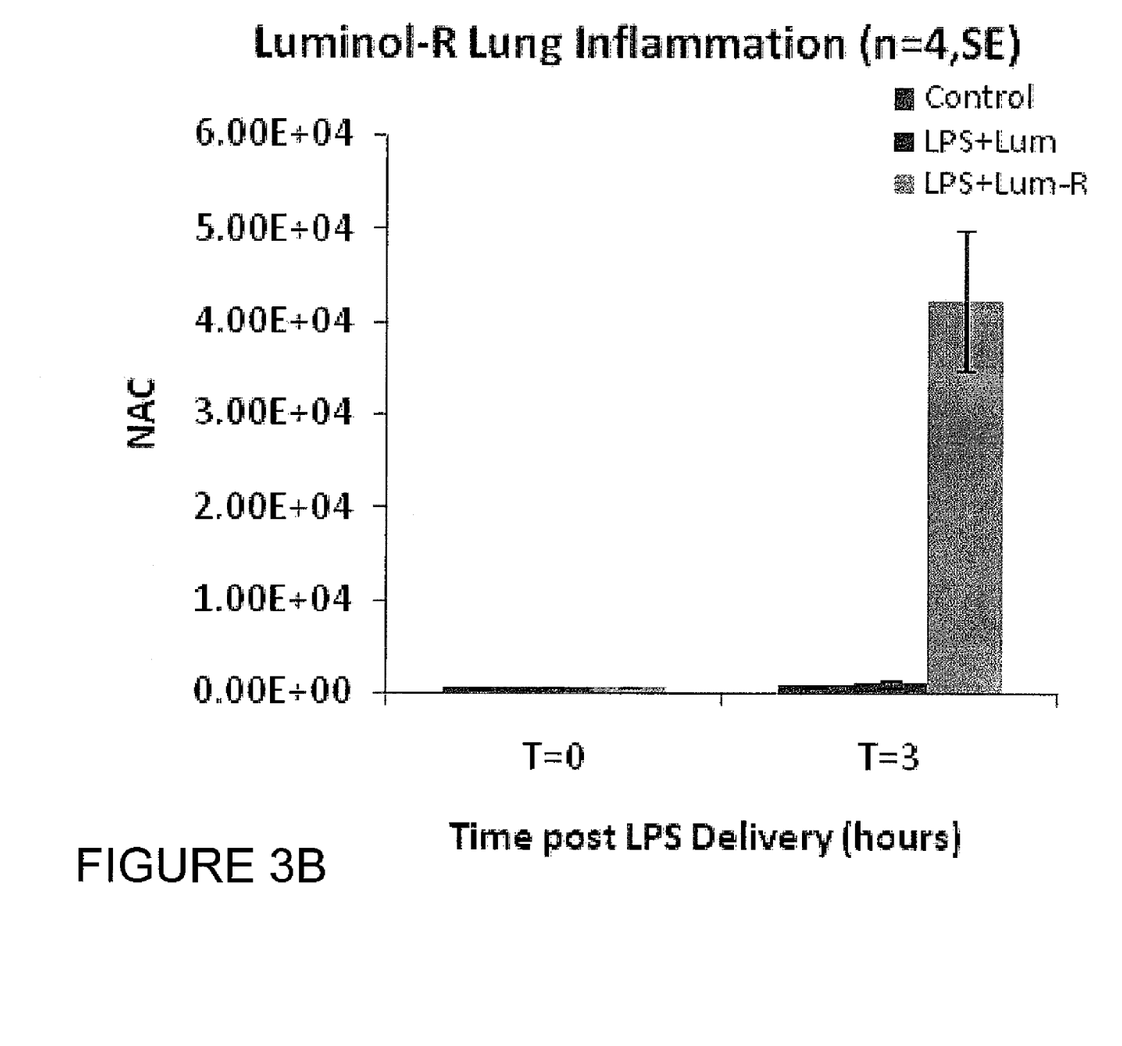
Figure 3C:
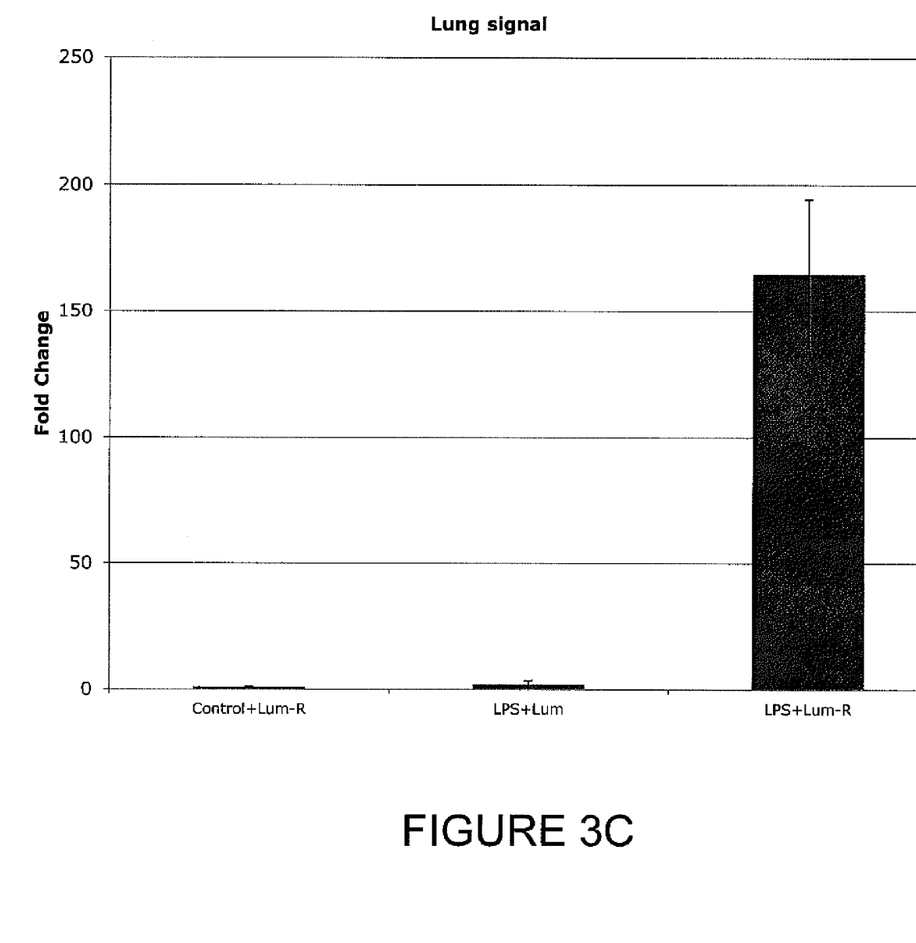

As shown in FIG. 3, NAC derived from free radical production was detected in the pulmonary tissues. When compared to non-treated control mice that were administered with a mixture of luminol and nanoparticles (Quantum dot 800), a 165 fold increase of NAC signal from the pulmonary tissues was observed. LPS treated mice that received luminol alone only showed two fold increase of lung signal as compared to control mice. We confirmed that the increase of detection sensitivity was due to red-shift of the luminol emitted light to NIR range, with a peak at 800 nm.

Figure 4A:
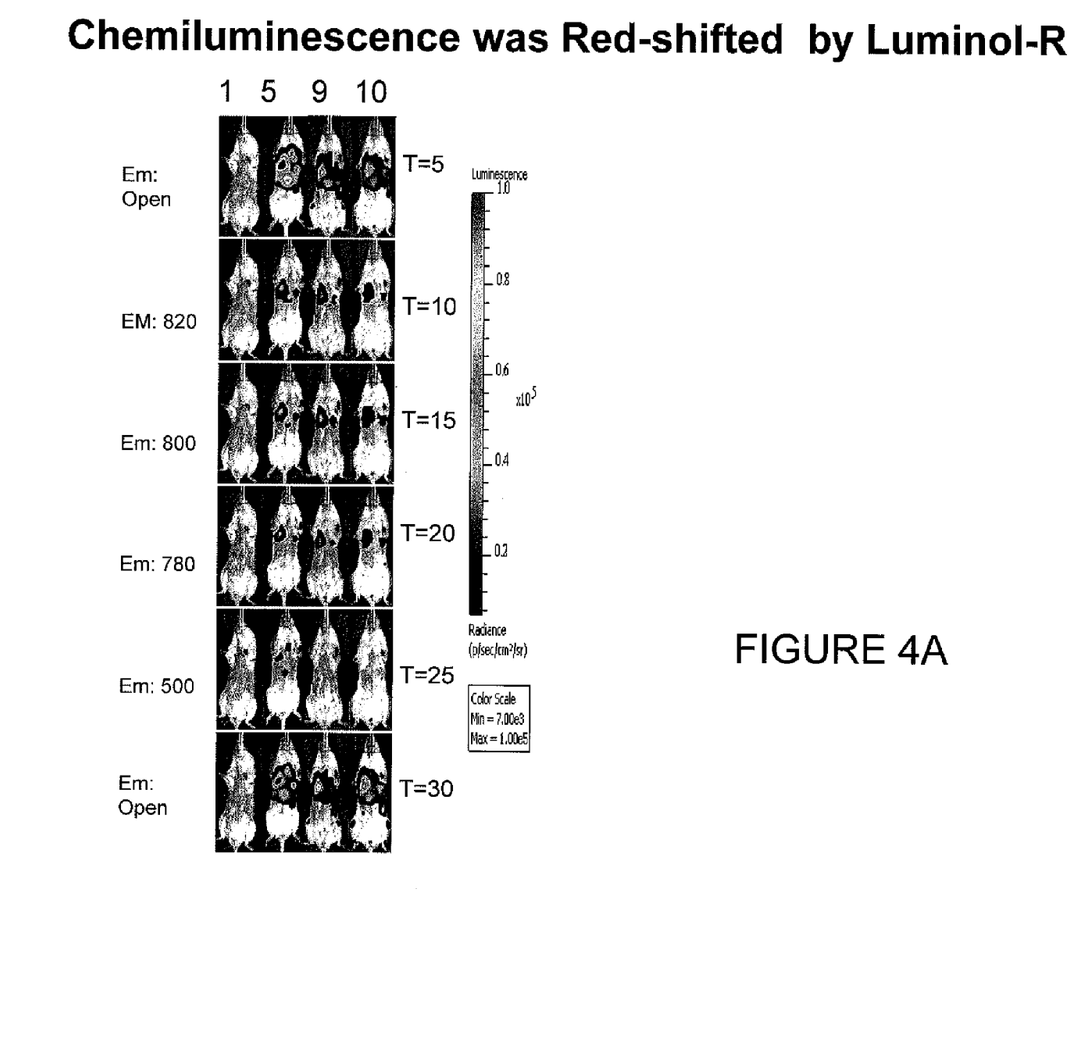
Figure 4B:
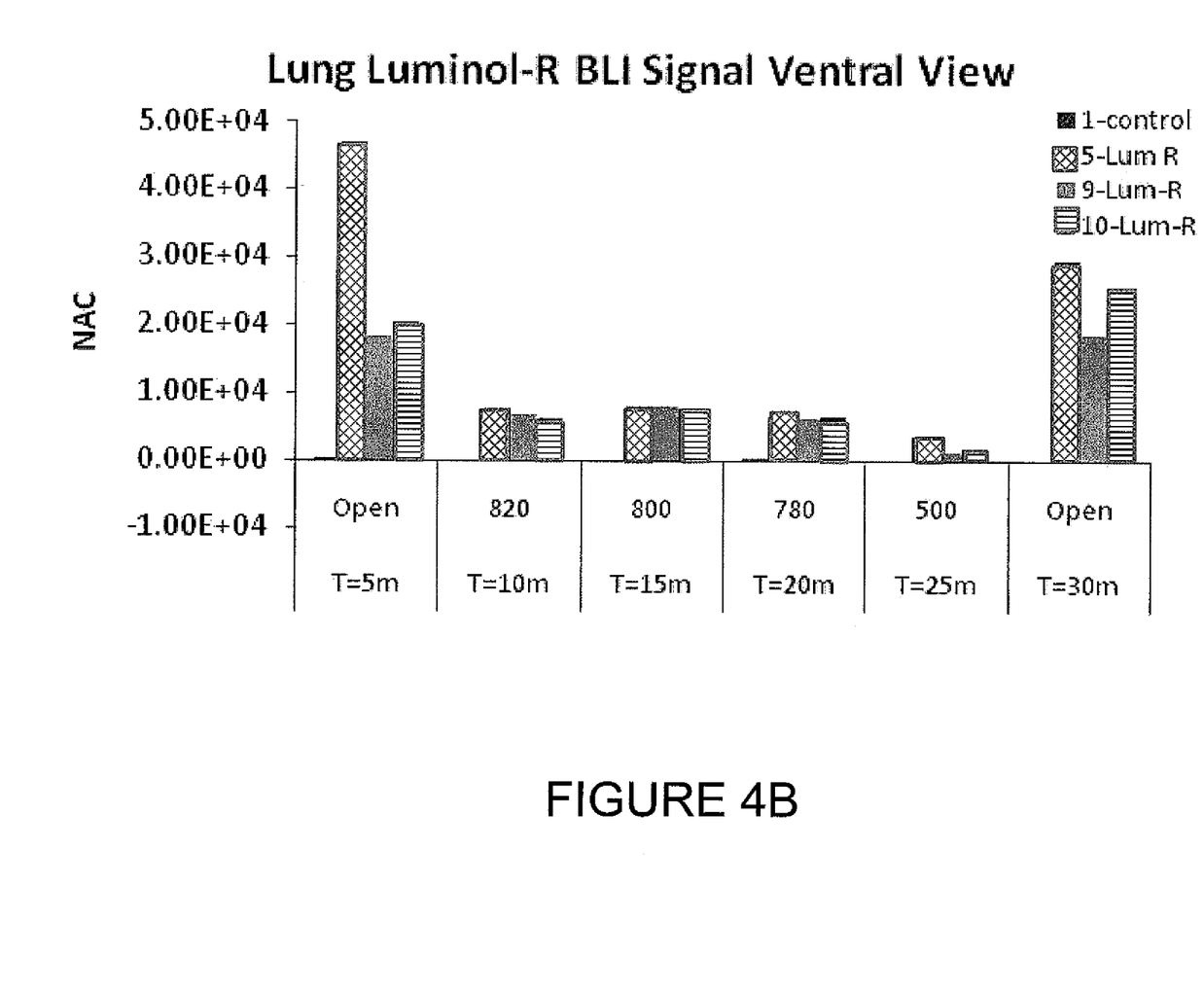

FIG. 4 shows NAC results obtained using various NIR filters. As shown, red-shifted NIR light was emitted from the lung following LPS/luminol/nanoparticle administration, with a peak emission at 800 nm. Using a 500 nm filter, the un-shifted light from luminol can also be detected, although at a lower level.

FIG. 5 shows NAC results with different NAC formulations, including luminol-R (luminol-Qdot800), Luminol-R700 (eFluor® 700NC, eBioSciences), and Luminol640 (nanoparticles from Optimeos Life Sciences).

Example 2

Detection of Tumors

As inflammation is involved in a broad range of disease process, including tumor development, the utility of the NAC compositions and methods was also tested for tumor detection. In a systemic metastases model through intracardiac injection of MDA-MB-231-luc tumor, metastatic tumor development in lungs and knee joints was also evaluated using NAC compositions. Briefly, a Nu/Nu mouse was injected intracardiacally with 1 million MDA-MB-231-luc2 tumor cells. At three weeks, the mouse was imaged with an IVIS spectrum following intraperitoneal injection of luciferin (150 mg/kg). At 24 hours after luciferin injection when the bioluminescence signal returned to a base line level, this mouse was injected intravenously with luminol. Tumor metastasis at the knee joint was detected. After another 24 hours when the signal returned to background level, a mixture of luminol and QD800 (Luminol-R, in PBS) was intravenously injected and the mouse was imaged at 5 minutes after the injection.

Figure 6:
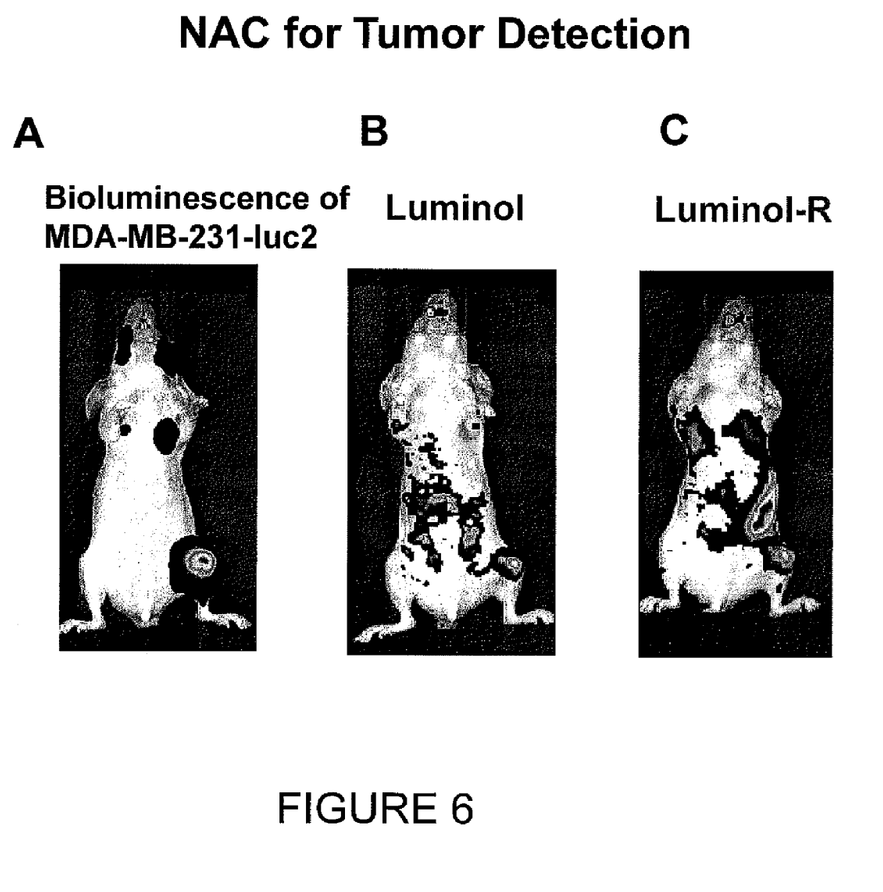

As shown in FIG. 6, bioluminescent tumor metastases was detected in the lungs, knee joints and cranial region following initial injection of luciferin and IVIS spectrum imaging (FIG. 6A). Tumor metastasis was also detecting using luminol alone (FIG. 6B). As shown in FIG. 6C, sensitive detection was achieved using NAC (luminol/nanoparticle) compositions as described herein. These signals correlated with tumor metastases in these loci, affirming that the tumor development triggered local inflammatory response and oxidative stress can be visualized with NAC at a much increased sensitivity over luminol. Strong NAC signal in the spleen intestines may indicate systemic inflammatory response in the mouse to tumor metastases. Thus, NAC imaging can non-discriminately detect oxidative stress in living animal.

Thus, compositions and methods as described herein can be used to detect enzymatic activity in living animals. Although preferred embodiments have been described in some detail, it is understood that obvious variations can be made without departing from the spirit and the scope of the disclosure.

What is claimed is:

1. An injectable composition consisting of a chemiluminescent enzymatic probe and an unconjugated near-infrared (NIR) nanoparticle, wherein the composition is injected into a live animal such that
    (i) the chemiluminescent enzymatic probe emits chemiluminescence in the presence of a product of endogenous enzyme activity in the live animal; and
    (ii) the NIR particle emits light upon exposure to the chemiluminescence emitted from the chemiluminescent probe.

2. The composition of claim 1, wherein the chemiluminescent enzymatic probe comprises luminol.

3. The composition of claim 1, wherein the NIR nanoparticle further comprises a targeting moiety.

4. The composition of claim 3, wherein the targeting moiety is selected from the group consisting of an antibody, an antibody fragment, an aptamer and a polypeptide.

5. A method of monitoring enzymatic activity in a live animal, the method comprising:
    administering the composition according to claim 1 into the live animal;
    detecting the light emitted from the light nanoparticle, thereby monitoring enzymatic activity in the live animal.

6. The method of claim 5 wherein the chemiluminescent enzymatic probe comprises luminol.

7. The method of claim 6, wherein ROS activity is monitored.

8. The method of claim 6, wherein a cancer is detected.

9. The method of claim 6, wherein the enzymatic activity is indicative of an inflammatory response.

10. The method of claim 9, wherein the inflammatory response is in the lungs.

11. The method of claim 6, wherein the enzymatic activity is indicative of the presence of a tumor or tumor metastases.

12. A method of detecting a cancer in a live animal, the method comprising:
    administering the composition according to claim 1 into the live animal;
    detecting the light emitted from the NIR nanoparticle, thereby monitoring the cancer in the live animal.

13. The method of claim 12, wherein the cancer is a solid tumor or a site of metastases.

14. A method, of monitoring enzymatic activity in a live animal, the method comprising:
    injecting the composition according to claim 1 into the live animal; and
    detecting the light emitted from the light nanoparticle, thereby monitoring enzymatic activity in the live animal.

15. The method of claim 14, wherein the chemiluminescent enzymatic probe comprises luminol.

16. The method of claim 14, wherein ROS activity is monitored.

17. The method of claim 14, wherein a cancer is detected.

18. The method of claim 14, wherein the enzymatic activity is indicative of an inflammatory response.

19. The method of claim 18, wherein the inflammatory response is in the lungs.

20. The method of claim 14, wherein the enzymatic activity is indicative of the presence of a tumor or tumor metastases.

21. A method of detecting a cancer in a live animal, the method comprising:
    injecting the composition of claim 1 into the live animal; and
    detecting the light emitted from the NIR nanoparticle, thereby monitoring the cancer in the live animal.

22. The method of claim 21, wherein the cancer is a solid tumor or a site of metastases.

* * * * *